US011449791B2

(12) United States Patent
Ramakrishnan

(10) Patent No.: US 11,449,791 B2
(45) Date of Patent: Sep. 20, 2022

(54) SYSTEM AND METHOD FOR MONITORING LAB PROCESSES AND PREDICTING THEIR OUTCOMES

(71) Applicant: Cognizant Technology Solutions India Pvt. Ltd, Chennai (IN)

(72) Inventor: Arvind Naganathan Ramakrishnan, Shrewsbury, MA (US)

(73) Assignee: COGNIZANT TECHNOLOGY SOLUTIONS INDIA PVT. LTD., Chennai (IN)

( * ) Notice: Subject to any disclaimer, the term of this patent is extended or adjusted under 35 U.S.C. 154(b) by 925 days.

(21) Appl. No.: 16/244,236

(22) Filed: Jan. 10, 2019

(65) Prior Publication Data

US 2020/0160214 A1  May 21, 2020

(30) Foreign Application Priority Data

Nov. 16, 2018 (IN) .............................. 201841043169

(51) Int. Cl.
| | |
|---|---|
| *G06N 20/00* | (2019.01) |
| *G16H 10/40* | (2018.01) |
| *G16H 40/20* | (2018.01) |
| *G06F 8/30* | (2018.01) |
| *G10L 15/22* | (2006.01) |
| *G06N 5/02* | (2006.01) |

(52) U.S. Cl.
CPC ............... *G06N 20/00* (2019.01); *G06F 8/30* (2013.01); *G06N 5/02* (2013.01); *G10L 15/22* (2013.01); *G16H 10/40* (2018.01); *G16H 40/20* (2018.01); *G10L 2015/223* (2013.01)

(58) Field of Classification Search
CPC .. G06N 5/02; G06N 20/00; G06F 8/30; G06F 3/167; G16H 10/40; G16H 40/20; G10L 15/22; G10L 2015/223
See application file for complete search history.

(56) References Cited

U.S. PATENT DOCUMENTS 5,854,278 A * 12/1998 Pandey ................ C07D 305/14
549/511
7,424,465 B2 * 9/2008 Schuppert .......... G05B 13/0205
706/45

(Continued)

FOREIGN PATENT DOCUMENTS

EP          1200839 A1    10/2012

*Primary Examiner* — Etienne P Leroux
(74) *Attorney, Agent, or Firm* — Cantor Colburn LLP

(57) ABSTRACT

A system for monitoring one or more lab processes and predicting their outcomes is provided. The system comprises a data acquisition module configured to acquire at least one of: ambient data and experimental data in real time from one or more lab resources and instruments. The system further comprises a process setup and monitoring module configured to receive the acquired data and facilitate setting-up and monitoring of one or more processes in real time utilizing the received data. The system furthermore comprises an experiment prediction module that is configured to obtain data from the data acquisition module and process setup and monitoring module. The experiment prediction module is further configured to employ one or more machine learning techniques on the obtained data to generate one or more patterns to predict outcomes of the one or more processes conducted in the lab in real time.

19 Claims, 3 Drawing Sheets

(56) References Cited

U.S. PATENT DOCUMENTS

| | | | |
|---|---|---|---|
| 2003/0074248 A1* | 4/2003 | Braud | G06Q 10/1093 |
| | | | 705/7.18 |
| 2012/0289434 A1* | 11/2012 | Urdea | C12Q 1/6883 |
| | | | 506/39 |
| 2014/0380284 A1* | 12/2014 | Rivkin | G06F 11/3668 |
| | | | 717/124 |
| 2015/0052502 A1* | 2/2015 | Faillaci, III | G06F 3/0482 |
| | | | 717/125 |
| 2018/0189449 A1* | 7/2018 | Karumba | G16H 10/60 |
| 2018/0352085 A1* | 12/2018 | Philbin | H04L 67/146 |
| 2019/0087519 A1* | 3/2019 | Mercury | G06N 20/00 |
| 2019/0377790 A1* | 12/2019 | Redmond | G06F 40/35 |
| 2019/0392926 A1* | 12/2019 | Koh | G06F 40/40 |
| 2020/0134639 A1* | 4/2020 | Canedo | G06Q 10/00 |
| 2020/0381131 A1* | 12/2020 | Toleti | G16H 40/60 |

* cited by examiner

SYSTEM AND METHOD FOR MONITORING LAB PROCESSES AND PREDICTING THEIR OUTCOMES

FIELD OF THE INVENTION

The present invention relates generally to lab processes. In particular, the present invention relates to a method and system for predicting outcomes of lab processes through real time monitoring of the processes and artificial intelligence techniques.

BACKGROUND OF THE INVENTION

Rising costs and declining approval rates are driving pharmaceutical and biotechnology companies to rethink on how they bring drugs to market. The approvals for New Molecular Entities (NMEs) are at a downward trend over the last few years despite an increase in the research and development spending. A substantial portion of this research and development spending goes for the lab operations which includes conducting various lab processes. However, these lab operations face serious issues in efficiency and productivity and that has resulted in the spiralling costs and NME drought. The main reason behind inefficient and less productive lab operations is the inability to monitor the heavily funded lab processes in real time and also to predict their outcomes. This inability can be attributed to a disparate Information and Technology (IT) application landscape in the labs, lack of real-time data of processes under execution, siloed data sets associated with the lab operations, challenges in extracting desired data from underlying legacy systems and instruments, and varied data formats that makes the monitoring of the processes and analysis of data for predicting outcomes an inefficient and expensive affair.

While there are solutions in the market that try to address one or more issues related to inability to monitor the lab processes in real time and to predict their outcomes, each of these solutions suffer from one or more drawbacks. Such drawbacks include inability to provide a connected lab environment that accommodates legacy lab systems and instruments, lack of standard data connections, and analytical capabilities without scalability.

In light of the above, there is a need for a solution that can use digital technologies to extract relevant data from underlying legacy lab systems and instruments, and other multiple sources in real-time. There is further a need for a solution that can allow monitoring of processes in real time. There is further a need for a solution that can efficiently analyse the extracted data to predict outcomes of processes performed in the labs.

SUMMARY OF THE INVENTION

In an embodiment of the present invention, a system for monitoring one or more lab processes and predicting their outcomes is provided. The system comprises a data acquisition module, a process setup and monitoring module, and an experiment prediction module. The data acquisition module is configured to acquire at least one of ambient data and experimental data in real time from one or more lab resources and instruments. The one or more lab resources and instruments comprise Internet of Things (IoT) enabled lab instruments, computer connected lab instruments, lab and enterprise systems, time series database systems, existing Application Programming Interfaces (APIs), content libraries, voice inputs from one or more lab technicians and investigators working in the lab, and data historians. In an embodiment of the present invention, the voice inputs from one or more lab technicians and investigators are acquired using an artificial intelligence based virtual lab assistant. The virtual lab assistant is further configured to guide the one or more technicians to follow a predefined protocol adopted by the lab for executing a process. Further, the virtual lab assistant applies employs a cognitive agent to perceive and act upon voice inputs.

The process setup and monitoring module is configured to receive the acquired data and facilitate setting-up and monitoring of one or more processes in real time utilizing the received data. The process setup and monitoring module is configured to setup the one or more processes using one or more recipes created by a recipe builder tool. The recipe builder tool is configured to create software codes associated with the one or more recipes with every user interaction. In an embodiment of the present invention, the recipe builder tool has customizable prebuilt templates of unit operations and parameters associated with the one or more recipes to setup the one or more recipes. The customization comprises editing properties of the prebuilt templates to make them compliant to one or more business requirements. Further, the one or more created recipes facilitate creation of one or more campaigns for one or more drug candidates, wherein campaign of the one or more campaigns have one or more lots. The one or more lots are monitored for variation in range values of the one or more parameters associated with the one or more processes. In an embodiment of the present invention, when status of a parameter of the one or more parameters varies from a predefined range of values alerts are triggered by the process setup and monitoring module.

In an embodiment of the present invention, the system further comprises a resource tracking module configured to obtain the data associated with the one or more lab resources and instruments and facilitate tracking, mapping and planning of the one or more lab resources and instruments using the obtained data, the resource tracking module is further configured to generate one or more reports on usage and efficiency of the one or more lab resources and instruments. The experiment prediction module configured to obtain data from the data acquisition module and process setup and monitoring module. The experiment prediction module is further configured to employ one or more machine learning techniques to generate one or more patterns to predict outcomes of the one or more processes conducted in the lab in real time. In an embodiment of the present invention, the system furthermore comprises a content library communicatively coupled to the experiment prediction module and configured to provide access to one or more internal and external content providers and tools to facilitate prediction of outcomes of lab processes.

In another embodiment of the present invention, a method for monitoring one or more lab processes and predicting their outcomes is provided. The method comprises acquiring at least one of ambient data and experimental data in real time from one or more lab resources and instruments. The one or more lab resources and instruments comprise Internet of Things (IoT) enabled lab instruments, computer connected lab instruments, lab and enterprise systems, time series database systems, existing Application Programming Interfaces (APIs), content libraries, voice inputs from one or more lab technicians and investigators working in the lab, and data historians.

The method further comprises setting up one or more processes in real time utilizing the acquired data, wherein the one or more recipes are set-up using one or more recipes generated by a recipe builder tool. The recipe builder tool is configured to create software codes associated with the one or more recipes with every user interaction. In an embodiment of the present invention, the recipe builder tool has customizable prebuilt templates of unit operations and parameters associated with the one or more recipes to setup the one or more recipes, further wherein the customization comprises editing properties of the prebuilt templates to make them compliant to one or more business requirements. Further, the one or more created recipes facilitate creation of one or more campaigns for one or more drug candidates, wherein campaign of the one or more campaigns have one or more lots. The one or more lots are monitored for variation in range values of the one or more parameters associated with the one or more processes. In an embodiment of the present invention, alerts are triggered when status of a parameter of the one or more parameters varies from a predefined range of values.

In yet another embodiment of the present invention, a non-transitory computer-readable medium having computer-readable program code stored thereon is provided. The computer-readable program code comprising instructions that when executed by a processor, cause the processor to acquire at least one of ambient data and experimental data in real time from one or more lab resources and instruments. The processor is further caused to setup up one or more processes in real time utilizing the acquired data, wherein the one or more recipes are set-up using one or more recipes generated by a recipe builder tool. The processor is furthermore caused to monitor the one or more processes in real time and predict outcomes of the one or more processes. In an embodiment of the present invention, one or more machine learning techniques are employed on the acquired data to generate one or more patterns to predict outcomes of the one or more processes conducted in the lab in real time.

BRIEF DESCRIPTION OF THE ACCOMPANYING DRAWINGS

The present invention is described by way of embodiments illustrated in the accompanying drawings wherein.

DETAILED DESCRIPTION OF THE INVENTION

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
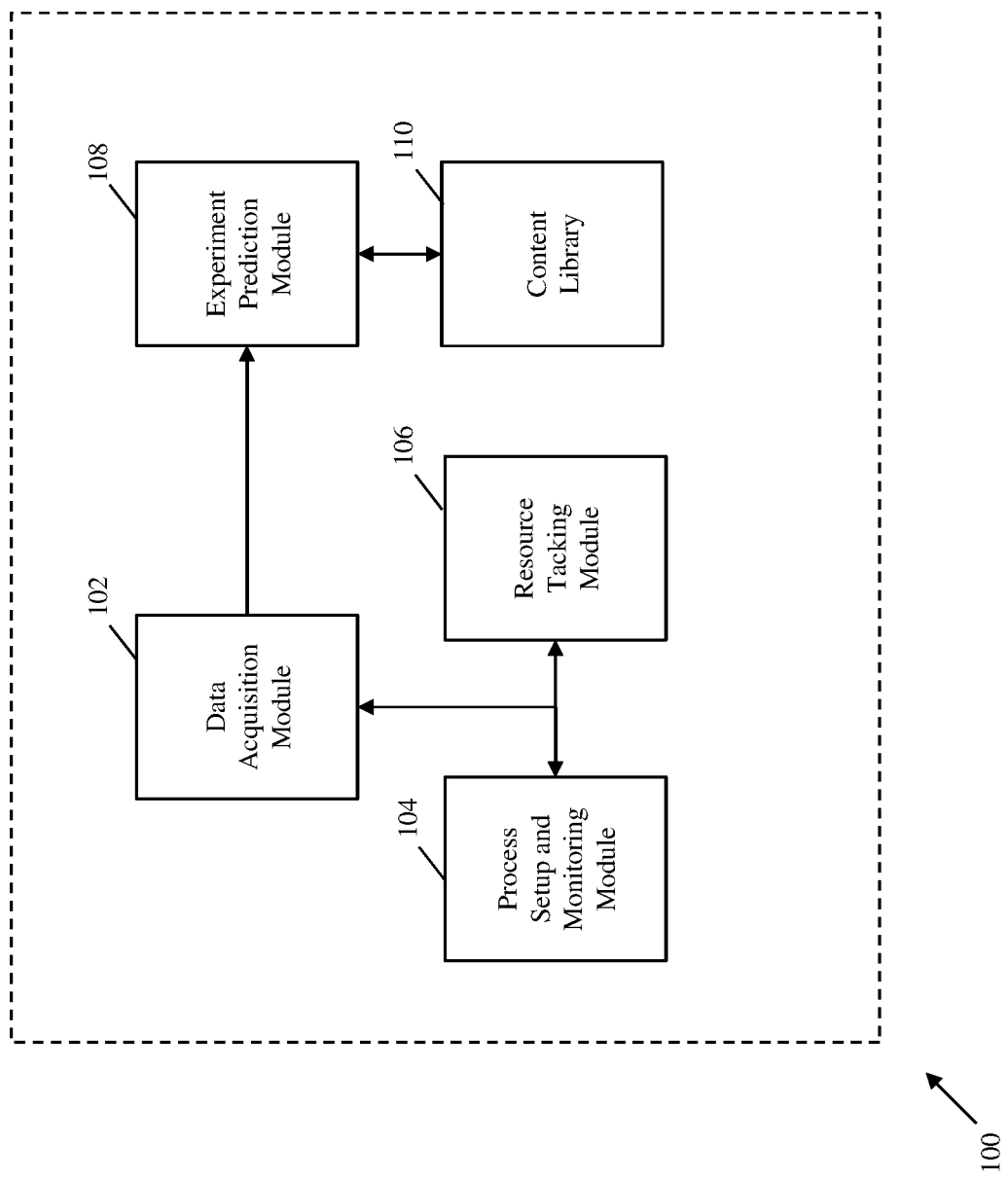
FIG. 1 is a block diagram illustrating a system for monitoring lab processes and predicting their outcomes in accordance with an embodiment of the present invention.

FIG. 1 is a block diagram illustrating a system 100 for monitoring one or more lab processes and predicting their outcomes in accordance with an embodiment of the present invention. The system 100 comprises a data acquisition module 102, a process setup and monitoring module 104, a resource tracking module 106, an experiment prediction module 108, and a content library 110. The system 100 may be employed for one or more lab environments including, without any limitation, chemistry research lab, bioprocess research lab, omics lab, pre-clinical animal lab, process lab, scale-up lab, manufacturing lab and quality assurance lab. In an embodiment of the present invention, the system 100 may be hosted in the one or more labs where the lab processes are conducted. In another embodiment of the present invention, the system 100 may be hosted at a remote location and may predict outcomes of the lab processes performed at the one or more labs using cloud based computing. Further, the system 100 may be accessed by one or more users including, without any limitation, lab system administrators, lab managers, lab scientists, lab technicians, and lab informatics analysts.

The data acquisition module 102 is configured to acquire various types of data from a plurality of lab resources including, without any limitation, Internet of Things (IoT) enabled lab instruments, computer connected lab instruments, lab and enterprise systems, time series database systems, existing Application Programming Interfaces (APIs), content libraries, voice inputs from one or more lab technicians and investigators working in the lab, and data historians. In an embodiment of the present invention, the various types of data may include, without any limitation, ambient data and experimental data. The ambient data may include temperature and pressure related information associated with the lab resources and instruments that may be used to determine health of the lab resources and instruments. The experimental data may be derived from execution of one or more processes and may be quantitative or qualitative results of a sample analysis. In various embodiments of the present invention, the data acquisition module 102 may acquire data using manual, automated, assisted and cognitive means. Further, the data may be acquired in real time, near-real-time, and as per requirement. Furthermore, the data acquisition module 102 may acquire data using a push model or pull model of data acquisition. In an embodiment of the present invention, the data acquisition module 102 may transform the data in the one or more predefined formats for further processing of data. The transformed data may be stored in one or more databases associated with the data acquisition module 102.

In an embodiment of the present invention, the voice data from the one or more technicians and investigators conducting processes in the lab may be collected using artificial intelligence based virtual lab assistant. The virtual lab assistant may facilitate collection of voice based notes when the one or more technicians and investigators are engaged in a task that requires extensive use of their hands and thus, recording data through a keypad, a computer mouse, etc. may result in contamination of experimental samples. For example, in situations when animals are being euthanized. In such conditions, the virtual lab assistant may facilitate capturing of the data through verbal commands. The captured data may be validated visually, using a computer screen, and may be modified or updated at a later stage or in real time. The virtual lab assistant may also allow the one or more technicians and investigators to access previously captured data and modify or update records. The virtual lab assistant may also guide the one or more technicians and investigators to follow a predefined protocol adopted by the lab for executing a process. The virtual lab assistant may also provide secure access to the one or more technicians and investigators through voice and/or device based recognition on individual devices. In an embodiment of the present invention, the recorded voice based data may be exported in form of, without any limitation, spreadsheets and Extensible Markup Language (XML) to the one or more databases associated with the data acquisition module 102.

Further in an embodiment of the present invention, the virtual lab assistant may comprise a listening layer, a processing layer, an integration layer and a user experience layer. The listening layer uses a voice capture device to capture voice from a user in real-time. The voice capture activity may be triggered by an authorized user by saying a designated and customizable wake word. The captured voice data is then transferred to the Processing layer. The processing layer may reside on a cloud infrastructure and is composed of a voice channel, a cognitive agent, and a domain rules engine. The voice channel is a customizable unit that uses the cognitive agent and the domain rules engine to perceive and act upon voice inputs. The cognitive agent is a learning agent that has problem solving rules and feedback mechanisms. The domain rules engine has a customizable list of curated scientific terms and ontologies available in at least one of public domain and exclusive private environments. Further, the integration layer brings together multiple agent-based actions and responses from the processing layer and integrates both the voice and text based user interaction. Finally, the user experience layer is the primary interface for users to interact with the virtual lab assistant. The user experience layer may facilitate a seamless access of text, visual and voice channels where a user may start with a voice-based interaction, move to a text-based interaction enabled by a visual screen and complete the action with a voice input. The user experience layer may also accommodate pause and resume of actions across both the voice and text based access methods.

The process setup and monitoring module 104 is configured to receive the data acquired by the data acquisition module 102 and facilitate setting-up, monitoring and scheduling of one or more processes utilizing the received data in real time. The one or more processes are the experiments that are conducted in one or more lab environments and each process has a plurality of steps. In an exemplary embodiment of the present invention, the steps of a process may comprise, without any limitation, taking a sample and bringing it to room temperature, moving the sample to a flask that activates or separates frozen cells by shaking the flask, and moving the sample to a bioreactor where a medium for cell growth is available that facilitates the cells to grow and multiply. Further, the one or more process are made up of one or more steps or unit operations and each unit operation of the one or more unit operations may have one or more parameters. Further, each parameter of the one or more parameters may have one or more ranges and each range of the one or more ranges may have one or more values.

In an embodiment of the present invention, the one or more processes may be built or set-up using one or more recipes generated by a recipe builder tool. In an exemplary embodiment of the present invention and in the context of a Bioprocess lab, a recipe may be defined as a virtual instance of one or more building blocks of a process for manufacturing a drug. The one or more building blocks of a process may comprise, without any limitation, a step of the process and a unit operation. Further, the recipe builder tool may provide an intuitive user interface to create the one or more recipes using information from the one or more lab resources and equipment, procedures, and formulas. The recipe builder tool may create software codes associated with the one or more recipes with every user interaction and thus, removing the need for custom code development for new recipe builds. Further, each recipe may be unique for an organization and the recipe builder tool may build a repository or a recipe list of all such created recipes.

In an embodiment of the present invention, the recipe builder tool may have customizable prebuilt templates of unit operations and parameters to setup the one or more recipes and in turn the one or more process. The prebuilt templates of unit operations and parameters may be customized to align with different lab environments and one or more business requirements. The customization may include editing of the properties of the prebuilt templates to make them compliant to one or more business requirements. The one or more recipes may further be customized by re-ordering the sequence of the steps or unit operations in the one or more recipes. Further, to generate the one or more recipes the users may perform actions like drag and drop or pick from a list of one or more master lists of unit operations and parameters and create one or more recipes. The master list facilitates reuse and standardization of the one or more elements in a lab. The drag and drop or pick-up from the master list also facilitates inheritance of properties in the new instances of recipes from the components of the master list.

The process setup and monitoring module 104 further facilitates tagging and commenting of the one or more recipes. The tagging and commenting improves discoverability of the one or more recipes in the recipe list, increases collaboration among the one or more users in the lab by encouraging social behaviours in the lab. The tagging of the one or more recipes may be achieved using standard or custom tags that may be visually differentiated. In an exemplary embodiment of the present invention, the standard tags may be derived from an internal or external list like Medical Subject Headings (MeSH). The MeSH is a comprehensive controlled vocabulary for the purpose of indexing journal articles, books, tags and comments in the field of life sciences.

Further, once the one or more recipes have been created, it can be used to create one or more campaigns when they are connected to the data acquisition module 102 for sourcing the data. In an embodiment of the present invention, the recipes are used to run campaigns for one or more drug candidates. Each campaign of the one or more campaigns may have one or more lots where each lot of the one or more lots may have the one or more unit operations. In an embodiment of the present invention, the one or more recipes may directly be connected to the one or more data sources, including the one or more databases associated with the data acquisition module 102, to obtain the data using a data queue. The data queue may identify all the unassigned data parcels and makes them available to be assigned to an end-point in the created one or more campaigns. The unassigned data parcels are raw data coming in from external sources like lab instruments, lab systems etc. The end-points are the unit operations or parameters setup within the one or more processes. Once all the relevant data points are connected, the one or more recipes may be launched as one or more campaigns. The one or more campaigns may run in several batches over time and each batch may be referred to as a lot. The one or more lots may be monitored using a digital dashboard for process compliance and to get a near-real-time status of the lots. In an exemplary embodiment of the present invention, the digital dashboard may be Red-Amber-Green (RAG) digital dashboard where red status for one or more parameters or unit operations may indicate that they are operating well beyond target ranges or limits. The Amber status may indicate that one or more parameters or unit operations are moving out of control ranges or limits. The green status may indicate absence of any issue in the one or more campaigns. The digital dashboard may further facilitate visual comparison across lots in one or more campaigns. The visual comparison may be of the variation in the range values of the one or more parameters. In an embodiment of the present invention, the process setup and monitoring module 104 may also log notifications when the RAG status of any of the unit operations and parameters changes. The notifications may be logged in a customizable zone with clear indicators of read or unread status. In an embodiment of the present invention, the process setup and monitoring module 104 may trigger alerts when status of any of the unit operations and parameters varies from a predefined range of values. The alerts may be sent to one or more users over one or more client devices as an email message or a text message.

The process setup and monitoring module 104 further facilitates scheduling of the one or more processes using the digital dashboard. The digital dashboard may facilitate assignment of the one or more processes to one or more owners and approvals of the states of the one or more processes by the assigned owners. In an embodiment of the present invention, the digital dashboard may implement role base access control for the one or more assigned owners. The one or more assigned owners may include lab managers, scientists, and informatics analysts.

The resource tracking module 106 is configured to obtain the data acquired by the data acquisition module 102 and further configured to provide a digital dashboard to facilitate tracking, mapping and planning of the various lab resources using the obtained data. The tracking of the lab resources may correspond to, without any limitation, collecting information on which of the resources are currently being used to identify the availability of the resources, location of the resources, utilization of the resources to understand how efficiently they are being utilized, and health of the resources to predict any possible breakdown of the resources. In an embodiment of the present invention, the resource tracking module 106 may track multiple types of resources including instruments, equipment, devices and people in the lab. Further, the mapping of the resources may correspond to, without any limitation, mapping the resources to the one or more created processes to perform lab processes. The ability to map the use of an instrument in an experiment or process may be achieved using a model that may create a physical instance as well as a virtual instance of the resource or instrument. Each physical instance of the instrument may generate a virtual instance when it is used in a process. Multiple virtual instances are connected to the original physical instance, which helps in the mapping and usage of that resource across different processes. The planning of the resources may correspond to, without any limitation, scheduling usage of the resources for future use based on their availability, priority and criticality of the one or more processes with which the resources have been mapped. Further, in an embodiment of the present invention, the digital dashboard that facilitates tracking, mapping and planning of the various lab resources may be RAG dashboard. The digital dashboard may also facilitate generation of one or more reports on usage and efficiency of the lab resources. In an embodiment of the present invention, the resource tracking module 106 may directly communicate with the plurality of lab resources to facilitate their tracking, mapping and planning.

The experiment prediction module 108 is configured to obtain data from the data acquisition module 102, process setup and monitoring module 104, and the content library 110 and facilitate prediction of outcomes of the processes conducted in the lab. The experiment prediction module 108 may also be configured to receive historical data associated with plurality of processes conducted in past in the lab and the data associated with the one or more created processes. The experiment prediction module 108 may analyse the obtained data in silos and may generate one or more patterns to analyse and predict the outcomes of the lab processes. In an embodiment of the present invention, the experiment prediction module 108 may generate one or more patterns by comparing two or more process runs for one or more characteristics of the processes. The experiment prediction module 108 may also make the obtained data available as a data digest to one or more external or third party statistical or analytical tools for predicting outcomes of the processes. The experiment prediction module 108 may also facilitate changes in the characteristics of the chosen processes for generating one or more patterns. In an embodiment of the present invention, the experiment prediction module 108 may provide an editor to facilitate changes in the characteristics of the chosen processes. The experiment prediction module 108 may also facilitate creation of one or more new patterns using drag and drop from one or more list features for the different characteristics of processes. In an embodiment of the present invention, the experiment prediction module 108 may employ one or more machine learning algorithms/techniques to generate the one or more patters to predict the outcomes of the lab processes. The experiment prediction module 108 may further be configured to determine probability of success of future lab processes based on the past performances or results. In an embodiment of the present invention, each experiment prediction may be executed in a separate container system that may be auto-scaled on a cloud-based hardware environment with minimal supervision. The system 100 also allow for metering and charge-back of the hardware used to individual processes or users, thus allowing the creation of an on-demand consumer platform.

The content library 110 is communicatively coupled to the experiment prediction module 108 and is configured to provide access to one or more internal and external content providers and tools to facilitate prediction of outcomes of lab processes. The content library 110 may use semantic content to generate hypothesis from the one or more internal and external content providers to facilitate predictions. The hypothesis may be generated using the semantic content and the experimental data digest along with the help of supervised learning systems. In an embodiment of the present invention, the content library 110 may employ one or more machine learning algorithms to automatically associate the one or more internal and external content providers and tools with the experiment prediction module 108. The interplay of the content library and the experiment prediction module 108 may also allow user supervision to intervention to add expert opinion and guidance to the automated hypothesis generation.

Thus, based on efficient acquisition of the desired from lab systems and instruments, real time monitoring of the processes performed in the labs, and prediction of outcomes of the processes based on real time monitoring and artificial intelligence techniques, the present invention reduces the time and effort in bringing a drug to the market. This reduction in time and effort in turn makes the whole process of bring the drug from the lab to the market more efficient as compared to known in the art solutions.

Figure 2:
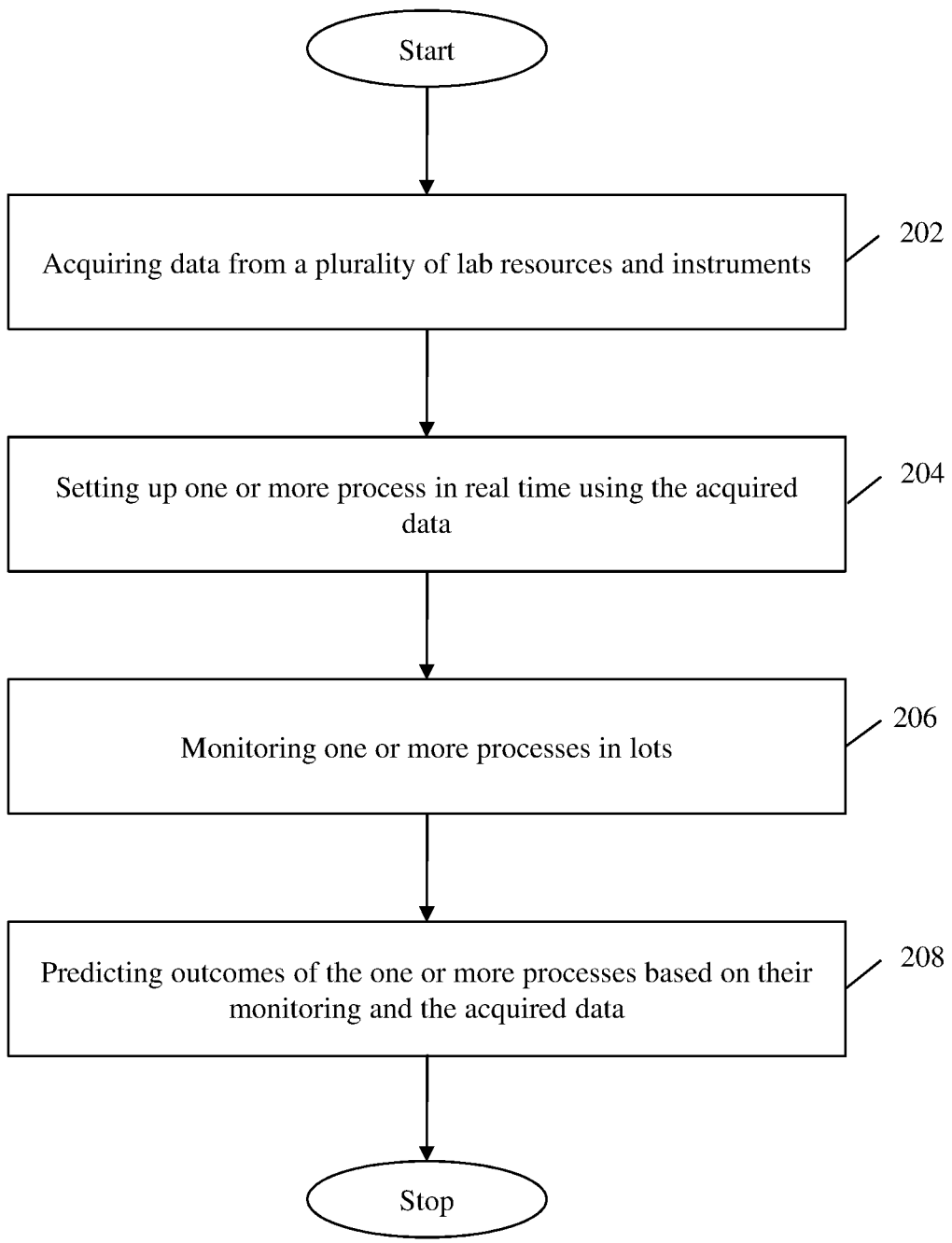
FIG. 2 is a flowchart illustrating a method for monitoring lab processes and predicting their outcomes in accordance with an embodiment of the present invention.

FIG. 2 is a flowchart illustrating a method for monitoring lab processes and predicting their outcomes in accordance with an embodiment of the present invention. The method may be employed for one or more lab environments including, without any limitation, chemistry research lab, bioprocess research lab, omics lab, pre-clinical animal lab, process lab, scale-up and technology transfer lab, manufacturing lab and quality assurance lab. At step 202, various types of data is acquired from a plurality of lab resources and instruments including, without any limitation, IoT enabled lab instruments, computer connected lab instruments, lab and enterprise systems, time series database systems, existing APIs, content libraries, voice inputs from one or more lab technicians and investigators working in the lab, and data historians. In an embodiment of the present invention, the various types of data may include, without any limitation, ambient data and experimental data. The ambient data may include temperature and pressure related information associated with the lab resources and instruments that may be used to determine health of the lab resources and instruments. The experimental data may be derived from execution of one or more processes and may be quantitative or qualitative results of a sample analysis. In various embodiments of the present invention, the data may be acquired using manual, automated, assisted and cognitive means. Further, the data may be acquired in real time, near-real-time, and as per requirement.

In an embodiment of the present invention, the voice data from the one or more technicians and investigators conducting processes in the lab may be collected using artificial intelligence based virtual lab assistant. The virtual lab assistant may facilitate collection of voice based notes when the one or more technicians and investigators are engaged in a task that requires extensive use of their hands and thus, recording data through a keypad, a computer mouse, etc. may result in contamination of experimental samples. For example, in situations when animals are being euthanized. In such conditions, the virtual lab assistant may facilitate capturing of the data through verbal commands. The captured data may be validated visually, using a computer screen, and may be modified or updated at a later stage or in real time. The virtual lab assistant may also allow the one or more technicians and investigators to access previously captured data and modify or update records. The virtual lab assistant may also guide the one or more technicians and investigators through the data capture process to follow a predefined protocol adopted by the lab. The virtual lab assistant may also provide secure access to the one or more technicians and investigators through voice and/or device based recognition on individual devices. In an embodiment of the present invention, the recorded voice based data may be exported in form of, without any limitation, spreadsheets and XML to the one or more databases.

At step 204, one or more process are set-up in real time using the acquired data. The one or more processes are the experiments that are conducted in one or more lab environments and each process has a plurality of steps. In an exemplary embodiment of the present invention, the steps of a process may comprise, without any limitation, taking a sample and bringing it to room temperature, moving the sample to a flask that activates or separates frozen cells by shaking the flask, and moving the sample to a bioreactor where a medium for cell growth is available that facilitates the cells to grow and multiply. Further, the one or more process are made up of one or more steps or unit operations and each unit operation of the one or more unit operations may have one or more parameters. Further, each parameter of the one or more parameters may have one or more ranges and each range of the one or more ranges may have one or more values. In an embodiment of the present invention, the one or more processes may set-up using one or more recipes generated by a recipe builder tool. In an exemplary embodiment of the present invention and in the context of a Bioprocess lab, a recipe may be defined as a virtual instance of one or more building blocks of a process for manufacturing a drug. The one or more building blocks of a process may comprise, without any limitation, a step of the process and a unit operation. Further, the recipe builder tool may provide an intuitive user interface to create the one or more recipes using information from the one or more lab resources and equipment, procedures, and formulas. The recipe builder tool may create software codes associated with the one or more recipes with every user interaction and thus, removing the need for custom code development for new recipe builds. Further, each recipe may be unique for an organization and the recipe builder tool may build a repository or a recipe list of all such created recipes.

The process setup step further comprises tagging and commenting of the one or more recipes. The tagging and commenting improves discoverability of the one or more recipes in the recipe list, increases collaboration among the one or more users in the lab by encouraging social behaviours in the lab. The tagging of the one or more recipes may be achieved using standard or custom tags that may be visually differentiated. In an exemplary embodiment of the present invention, the standard tags may be derived from an internal or external list like MeSH.

Further, once the one or more recipes have been created, the recipes are used to create more campaigns by feeding the acquired data to the one or more recipes. In an embodiment of the present invention, the recipes are used to run campaigns for one or more drug candidates. Each campaign of the one or more campaigns may have one or more lots where each lot of the one or more lots may have the one or more unit operations. In an embodiment of the present invention, the one or more recipes may directly be connected to the one or more data sources to obtain the data using a data queue. The data queue may identify all the unassigned data parcels and makes them available to be assigned to an end-point in the created one or more campaigns. The unassigned data parcels are raw data coming in from external sources like lab instruments, lab systems etc. The end-points are the unit operations or parameters setup within the one or more processes. Once all the relevant data points are connected, the one or more recipes may be launched as one or more campaigns. The one or more campaigns may run in several batches over time and each batch may be referred to as a lot.

At step 206, one or more processes in the form of lots are monitored. In an embodiment of the present invention, the one or more lots may be monitored using a digital dashboard for process compliance and to get a near-real-time status of the lots. In an exemplary embodiment of the present invention, the digital dashboard may be Red-Amber-Green (RAG) digital dashboard where red status for one or more parameters or unit operations of the one more processes may indicate that they are operating well beyond target ranges or limits. The Amber status may indicate that one or more parameters or unit operations of the one or more processes are moving out of control ranges or limits. The green status may indicate absence of any issue in the one or more campaigns. The digital dashboard may further facilitate visual comparison across lots in one or more campaigns. The visual comparison may be of the variation in the range values of the one or more parameters. In an embodiment of the present invention, one or more notifications may be logged when the RAG status of any of the unit operations and parameters changes. The notifications may be logged in a customizable zone with clear indicators of read or unread status. In an embodiment of the present invention, alerts may be triggered when status of any of the unit operations and parameters changes. The alerts may be sent to one or more users over one or more client devices as an email message or a text message.

At step 208, outcomes of the one or more processes conducted in the lab are predicted based on their monitoring and the use of the acquired data. In an embodiment of the present invention, one or more patterns are generated using the monitored values of the one or more parameters and acquired data to analyse and predict the outcomes of the lab processes. The one or more patterns may be generated by comparing two or more process runs for one or more characteristics of the processes. In an embodiments of the present invention, one or more machine learning algorithms may be employed to generate the one or more patters to predict the outcomes of the lab processes.

Figure 3:
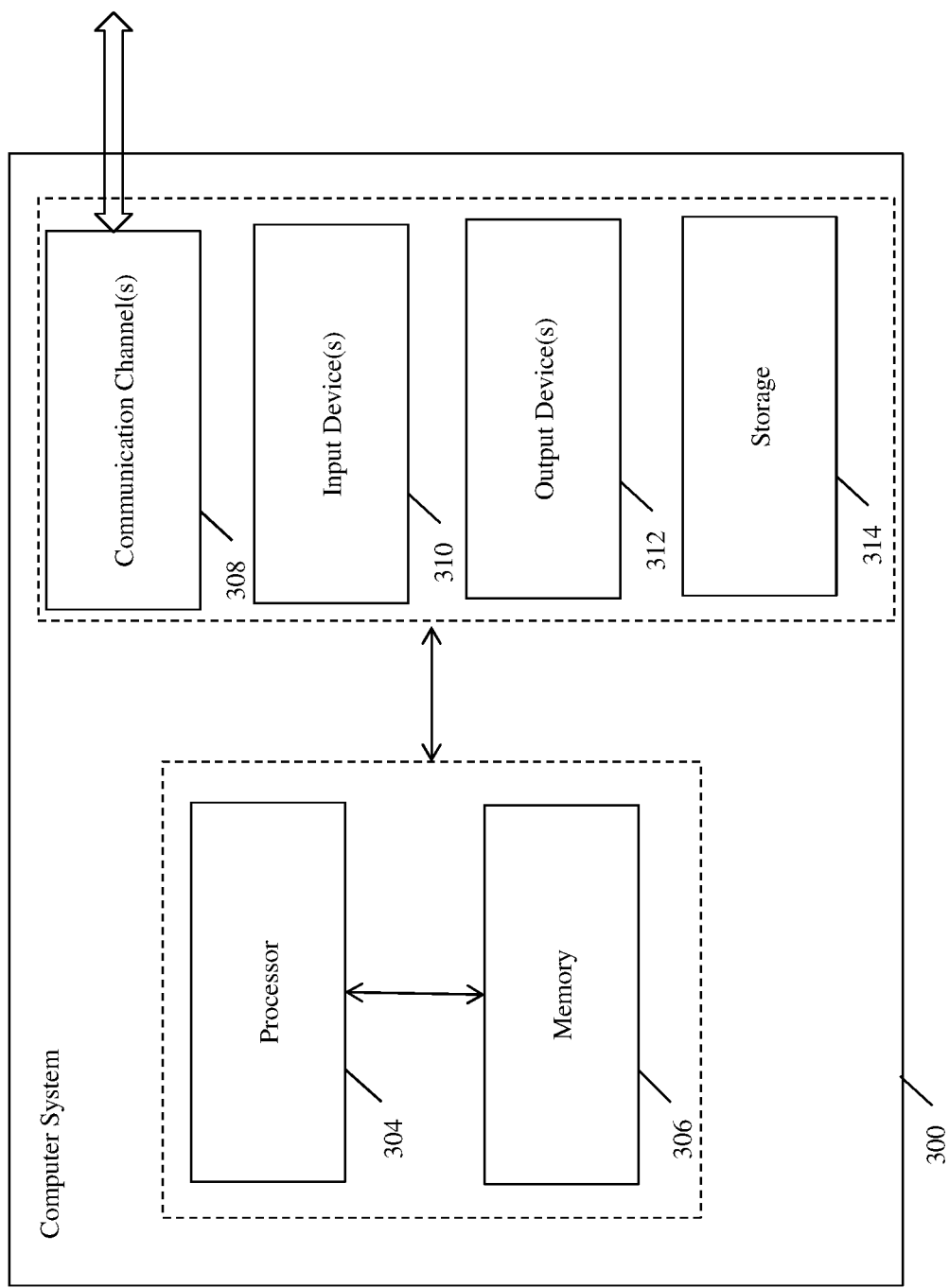
FIG. 3 illustrates an exemplary computer system in which various embodiments of the present invention may be implemented.

FIG. 3 illustrates an exemplary computer system in which various embodiments of the present invention may be implemented.

The computer system 302 comprises a processor 304 and a memory 306. The processor 304 executes program instructions and may be a physical processor. The processor 304 may also be a virtual processor. The computer system 302 is not intended to suggest any limitation as to scope of use or functionality of described embodiments. For example, the computer system 302 may include, but not limited to, a general-purpose computer, a programmed microprocessor, multi-core Graphics Processing Unit (GPU) to run deep learning models, a micro-controller, a peripheral integrated circuit element, and other devices or arrangements of devices that are capable of implementing the steps that constitute the method of the present invention. In an embodiment of the present invention, the memory 306 may store software for implementing various embodiments of the present invention. The computer system 302 may have additional components. For example, the computer system 302 includes one or more communication channels 308, one or more input devices 310, one or more output devices 312, and storage 314. An interconnection mechanism (not shown) such as a bus, controller, or network, interconnects the components of the computer system 302. In various embodiments of the present invention, operating system software (not shown) provides an operating environment for various software executing in the computer system 302, and manages different functionalities of the components of the computer system 302.

The communication channel(s) 308 allow communication over a communication medium to various other computing entities. The communication medium provides information such as program instructions, or other data in a communication media. The communication media includes, but not limited to, wired or wireless methodologies implemented with an electrical, optical, RF, infrared, acoustic, microwave, Bluetooth or other transmission media.

The input device(s) 310 may include, but not limited to, a keyboard, mouse, pen, joystick, trackball, a voice device, a scanning device, or any another device that is capable of providing input to the computer system 302. In an embodiment of the present invention, the input device(s) 310 may be a sound card or similar device that accepts audio input in analog or digital form. The output device(s) 312 may include, but not limited to, a user interface on CRT or LCD, printer, speaker, CD/DVD writer, or any other device that provides output from the computer system 302.

The storage 314 may include, but not limited to, magnetic disks, magnetic tapes, CD-ROMs, CD-RWs, DVDs, flash drives or any other medium which can be used to store information and can be accessed by the computer system 302. In various embodiments of the present invention, the storage 314 contains program instructions for implementing the described embodiments.

The present invention may suitably be embodied as a computer program product for use with the computer system 302. The method described herein is typically implemented as a computer program product, comprising a set of program instructions which is executed by the computer system 302 or any other similar device. The set of program instructions may be a series of computer readable codes stored on a tangible medium, such as a computer readable storage medium (storage 314), for example, diskette, CD-ROM, ROM, flash drives or hard disk, or transmittable to the computer system 302, via a modem or other interface device, over either a tangible medium, including but not limited to optical or analogue communications channel(s) 308. The implementation of the invention as a computer program product may be in an intangible form using wireless techniques, including but not limited to microwave, infrared, Bluetooth or other transmission techniques. These instructions can be preloaded into a system or recorded on a storage medium such as a CD-ROM, or made available for downloading over a network such as the internet or a mobile telephone network. The series of computer readable instructions may embody all or part of the functionality previously described herein.

The present invention may be implemented in numerous ways including as a system, a method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

I claim:

1. A system for monitoring one or more lab processes and predicting outcomes, the system comprising:
    a data acquisition module configured to acquire at least one of: ambient data and experimental data in real time from one or more lab resources and instruments;
    a process setup and monitoring module configured to receive the acquired data and facilitate setting-up of one or more processes in real time utilizing the acquired data, wherein the one or more processes are setup using one or more recipes created by a recipe builder tool, and wherein the recipe builder tool has customizable prebuilt templates of unit operations and parameters associated with the one or more recipes to setup the one or more recipes; and an experiment prediction module configured to:
obtain data from the data acquisition module and process setup and monitoring module; and
employ one or more machine learning techniques to generate one or more patterns to predict outcomes of the one or more processes conducted in the lab in real time.

2. The system of claim 1, wherein the one or more lab resources and instruments comprise Internet of Things (IoT) enabled lab instruments, computer connected lab instruments, lab and enterprise systems, time series database systems, existing Application Programming Interfaces (APIs), content libraries, voice inputs from one or more lab technicians and investigators working in the lab, and data historians.

3. The system of claim 2, wherein the voice inputs from one or more lab technicians and investigators are acquired using an artificial intelligence based virtual lab assistant.

4. The system of claim 3, wherein the virtual lab assistant is further configured to guide the one or more technicians to follow a predefined protocol adopted by the lab for capturing the voice data.

5. The system of claim 3, wherein the virtual lab assistant employs a cognitive agent to perceive and act upon voice inputs.

6. The system of claim 1, wherein the recipe builder tool is configured to create software codes associated with the one or more recipes with every user interaction.

7. The system of claim 1, wherein the recipe builder tool edits properties of the customizable prebuilt templates to make them compliant to one or more business requirements.

8. The system of claim 1, wherein the one or more created recipes facilitate creation of one or more campaigns for one or more drug candidates, wherein campaign of the one or more campaigns have one or more lots.

9. The system of claim 8, wherein the one or more lots are monitored for variation in range values of the one or more parameters associated with the one or more processes.

10. The system of claim 9, wherein alerts are triggered by the process setup and monitoring module when status of a parameter of the one or more parameters varies from a predefined range of values.

11. The system of claim 1, further comprises a resource tracking module configured to obtain the data associated with the one or more lab resources and instruments and facilitate tracking, mapping and planning of the one or more lab resources and instruments using the obtained data, the resource tracking module is further configured to generate one or more reports on usage and efficiency of the one or more lab resources and instruments.

12. The system of claim 1, further comprises a content library communicatively coupled to the experiment prediction module and configured to provide access to one or more internal and external content providers and tools to facilitate prediction of outcomes of lab processes.

13. A method for monitoring one or more lab processes and predicting outcomes, the method comprises:
acquiring at least one of: ambient data and experimental data in real time from one or more lab resources and instruments;

setting up one or more processes in real time utilizing the acquired data, wherein the one or more processes are setup using one or more recipes created by a recipe builder tool, and wherein the recipe builder tool has customizable prebuilt templates of unit operations and parameters associated with the one or more recipes to setup the one or more recipes;
monitoring the one or more processes in real time; and
predicting outcomes of the one or more processes based on their the monitoring and the acquired data, wherein one or more machine learning techniques are employed to generate one or more patterns to predict the outcomes of the one or more processes conducted in the lab in real time.

14. The method of claim 13, wherein the one or more lab resources and instruments comprise Internet of Things (IoT) enabled lab instruments, computer connected lab instruments, lab and enterprise systems, time series database systems, existing Application Programming Interfaces (APIs), content libraries, voice inputs from one or more lab technicians and investigators working in the lab, and data historians.

15. The method of claim 13, wherein the recipe builder tool is configured to create software codes associated with the one or more recipes with every user interaction.

16. The method of claim 13, wherein properties of the customizable prebuilt templates are edited to make them compliant to one or more business requirements.

17. The method of claim 13, wherein the one or more created recipes facilitate creation of one or more campaigns for one or more drug candidates, wherein campaign of the one or more campaigns have one or more lots, further wherein the one or more lots are monitored for variation in range values of the one or more parameters associated with the one or more processes.

18. The method of claim 17, wherein alerts are triggered when status of a parameter of the one or more parameters varies from a predefined range of values.

19. A computer program product comprising:
a non-transitory computer-readable medium having computer-readable program code stored thereon, the computer-readable program code comprising instructions that when executed by a processor, cause the processor to:
acquire at least one of: ambient data and experimental data in real time from one or more lab resources and instruments;
setup up one or more processes in real time utilizing the acquired data, wherein the one or more processes are setup using one or more recipes created by a recipe builder tool, and wherein the recipe builder tool has customizable prebuilt templates of unit operations and parameters associated with the one or more recipes to setup the one or more recipes;
monitor the one or more processes in real time; and
predict outcomes of the one or more processes based on their the monitoring and the acquired data, wherein one or more machine learning techniques are employed to generate one or more patterns to predict the outcomes of the one or more processes conducted in the lab in real time.

* * * * *